(12) United States Patent
Tallarida et al.

(10) Patent No.: US 7,311,702 B2
(45) Date of Patent: Dec. 25, 2007

(54) ABLATION TECHNOLOGY FOR CATHETER BASED DELIVERY SYSTEMS

(75) Inventors: Steven J. Tallarida, Mansfield, MA (US); Scott M. Epstein, Natick, MA (US); Kenneth Eliasen, Bridgewater, MA (US); Steven Ek, Bolton, MA (US)

(73) Assignee: STD Manufacturing, Inc., Stoughton, MA (US)

( * ) Notice: Subject to any disclaimer, the term of this patent is extended or adjusted under 35 U.S.C. 154(b) by 703 days.

(21) Appl. No.: 10/348,396

(22) Filed: Jan. 21, 2003

(65) Prior Publication Data

US 2003/0195504 A1 Oct. 16, 2003

Related U.S. Application Data

(60) Provisional application No. 60/349,813, filed on Jan. 18, 2002.

(51) Int. Cl.
*A61B 18/04* (2006.01)

(52) U.S. Cl. ............... 606/33; 607/96; 607/100; 607/101; 607/156; 600/373; 600/427; 600/439

(58) Field of Classification Search ........... 600/373, 600/374, 407, 430, 425, 427, 547; 607/96–101, 607/154–156; 606/33
See application file for complete search history.

(56) References Cited

U.S. PATENT DOCUMENTS

| | | | | |
|---|---|---|---|---|
| 5,057,105 A | | 10/1991 | Malone et al. | 606/28 |
| 5,246,438 A | * | 9/1993 | Langberg | 606/33 |
| 5,334,193 A | * | 8/1994 | Nardella | 606/41 |
| 5,348,554 A | * | 9/1994 | Imran et al. | 606/41 |
| 5,405,346 A | * | 4/1995 | Grundy et al. | 606/41 |
| 5,588,432 A | * | 12/1996 | Crowley | 600/439 |
| 5,693,082 A | * | 12/1997 | Warner et al. | 607/156 |
| 5,728,143 A | * | 3/1998 | Gough et al. | 607/101 |
| 5,868,737 A | | 2/1999 | Taylor et al. | 606/34 |
| 6,002,968 A | * | 12/1999 | Edwards | 607/101 |
| 6,007,570 A | * | 12/1999 | Sharkey et al. | 607/96 |
| 6,010,499 A | | 1/2000 | Cobb | 606/40 |
| 6,186,147 B1 | | 2/2001 | Cobb | 128/898 |
| 6,200,268 B1 | | 3/2001 | Vince et al. | 600/443 |

(Continued)

FOREIGN PATENT DOCUMENTS

GB WO9965378 12/1999

OTHER PUBLICATIONS

Claims from U.S. Appl. No. 09/719,970, filed Dec. 18, 2000.

(Continued)

*Primary Examiner*—Eleni Mantis Mercader
*Assistant Examiner*—Sanjay Cattungal
(74) *Attorney, Agent, or Firm*—Grossman, Tucker, Perreault & Pfleger PLLC

(57) ABSTRACT

A catheter based delivery system may be used for both therapeutic and diagnostic applications. The catheter based delivery system includes a catheter having a distal end. The distal end of the catheter includes several electrodes that can emit a radio frequency waveform, and may receive a signal representative of an impedance of material in the exposed to the radio frequency waveform. The radio frequency waveform may also be applied to ablate specifically targeted material exposed to the radio frequency waveform. The several electrodes may be configured as an antenna.

22 Claims, 16 Drawing Sheets

U.S. PATENT DOCUMENTS

| | | | |
|---|---|---|---|
| 6,245,020 B1 * | 6/2001 | Moore et al. | 600/466 |
| 6,321,121 B1 | 11/2001 | Zelickson et al. | 607/101 |
| 6,322,559 B1 | 11/2001 | Daulton et al. | 606/41 |
| 6,381,350 B1 | 4/2002 | Klingensmith et al. | 382/128 |
| 6,635,054 B2 * | 10/2003 | Fjield et al. | 606/27 |
| 6,638,222 B2 * | 10/2003 | Chandrasekaran et al. | 600/439 |
| 6,673,068 B1 * | 1/2004 | Berube | 606/33 |
| 6,689,128 B2 * | 2/2004 | Sliwa et al. | 606/41 |
| 6,862,467 B2 * | 3/2005 | Moore et al. | 600/407 |
| 2001/0001314 A1 * | 5/2001 | Davison et al. | 606/41 |
| 2001/0023365 A1 * | 9/2001 | Medhkour et al. | 607/99 |
| 2002/0013581 A1 * | 1/2002 | Edwards et al. | 606/41 |
| 2002/0068930 A1 * | 6/2002 | Tasto et al. | 606/32 |
| 2002/0099428 A1 | 7/2002 | Kaufman | 607/101 |
| 2002/0133148 A1 * | 9/2002 | Daniel et al. | 606/34 |
| 2003/0004430 A1 | 1/2003 | Casscells et al. | 600/545 |
| 2003/0028114 A1 | 2/2003 | Casscells, III et al. | 600/474 |
| 2003/0036713 A1 | 2/2003 | Bouton et al. | 600/587 |
| 2003/0050557 A1 | 3/2003 | Susil et al. | 600/424 |
| 2003/0055418 A1 * | 3/2003 | Tasto et al. | 606/32 |
| 2003/0088245 A1 * | 5/2003 | Woloszko et al. | 606/41 |
| 2003/0114848 A1 | 6/2003 | Cobb | 606/48 |
| 2003/0135110 A1 * | 7/2003 | Leussler | 600/422 |
| 2004/0138652 A1 * | 7/2004 | Berube | 606/33 |

OTHER PUBLICATIONS

Amendment from U.S. Appl. No. 09/719,970, filed Dec. 18, 2000.
Lerner Research Institute, The Cleveland Clinic Foundation, Cleveland, Ohio 44195 "Real-time 3D Reconstruction", Whitaker Biomedical Laboratory, pp. 1-3, 1-6, 1-3, undated.

* cited by examiner

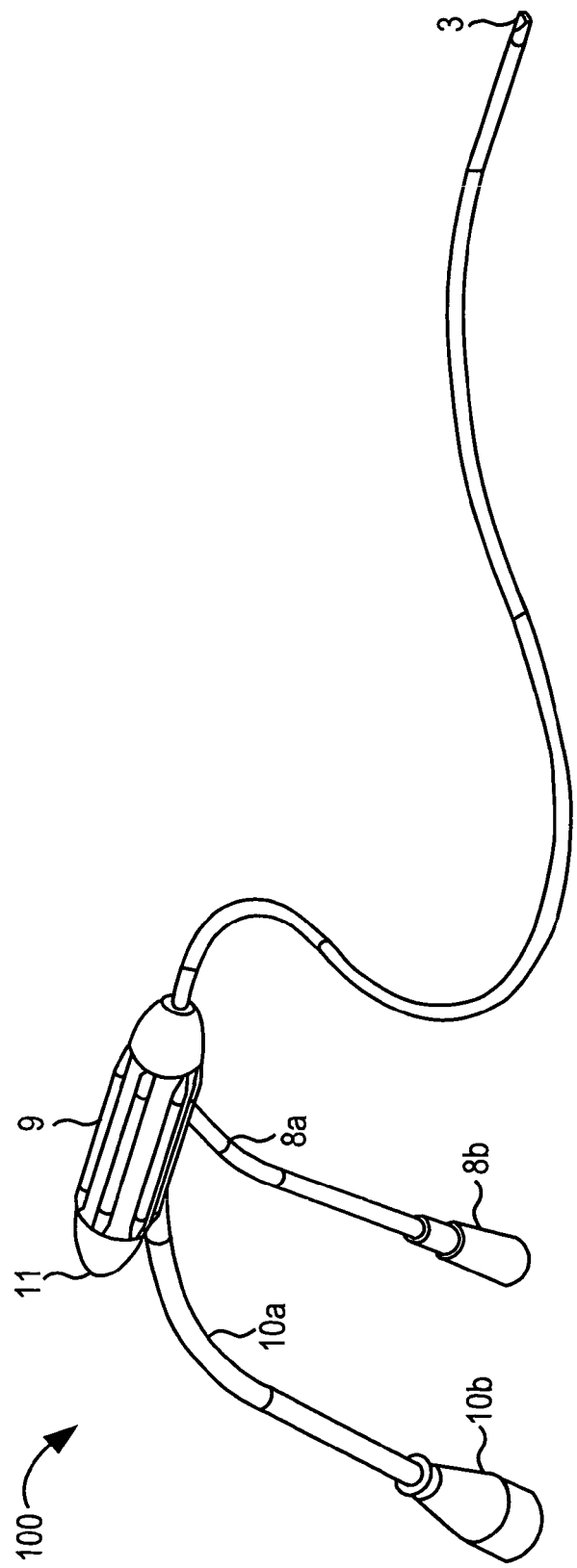

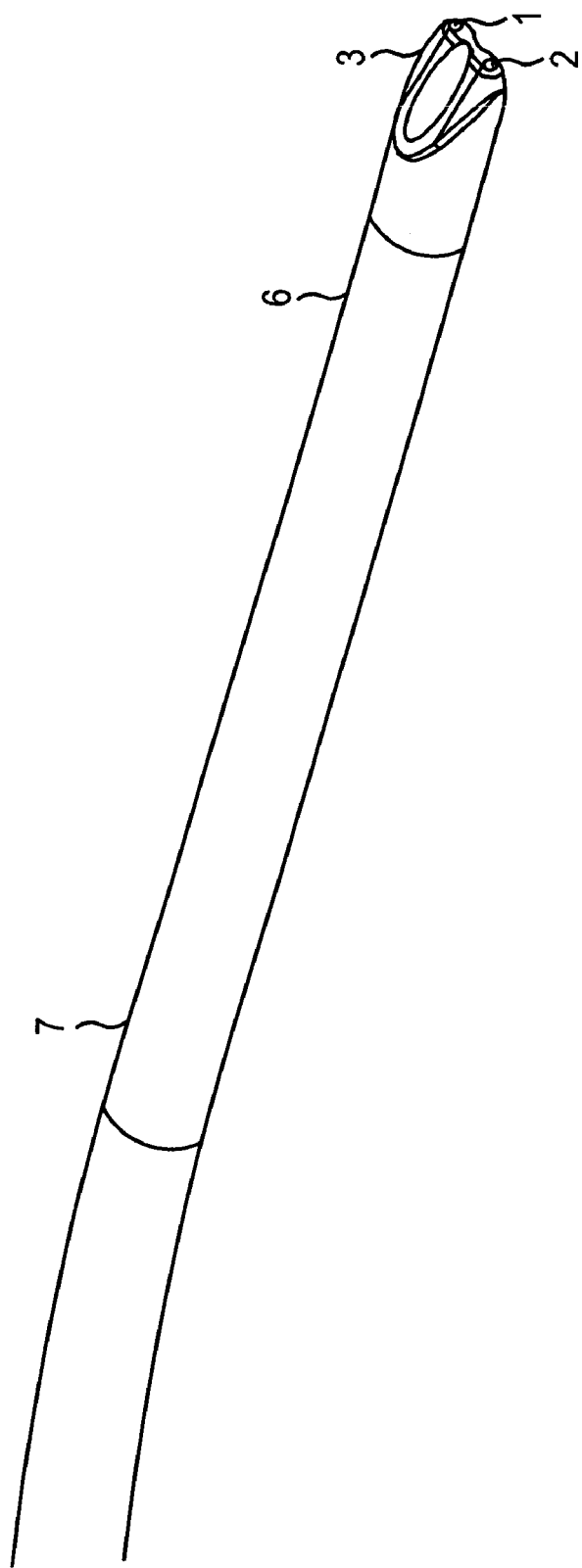

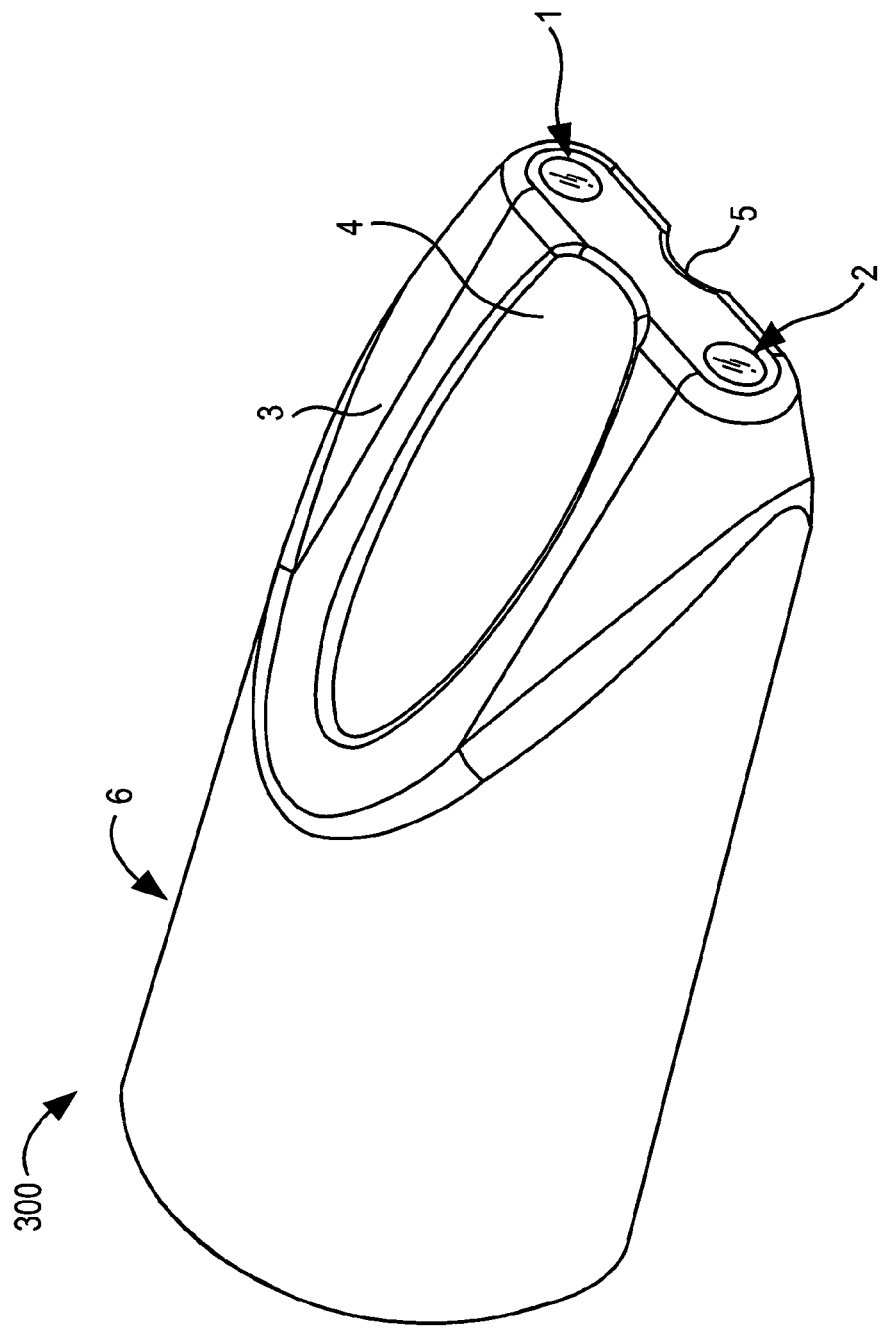

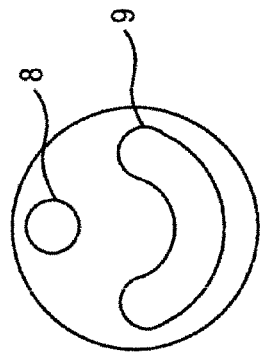
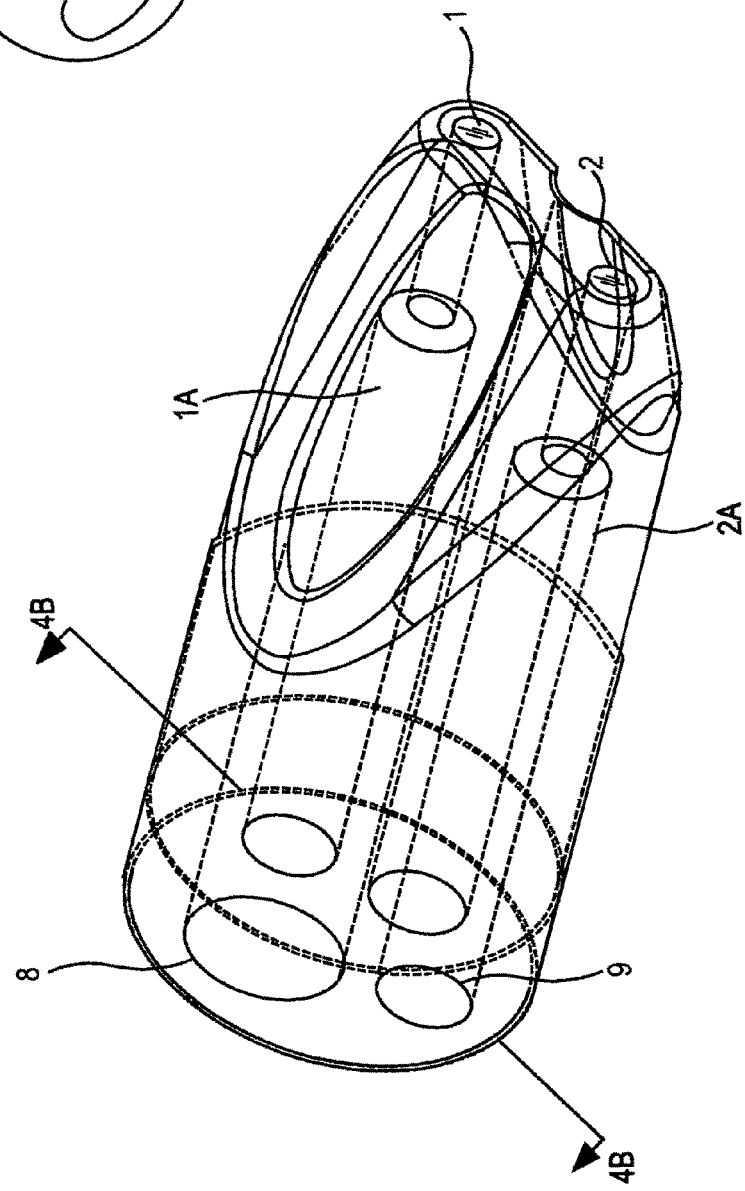

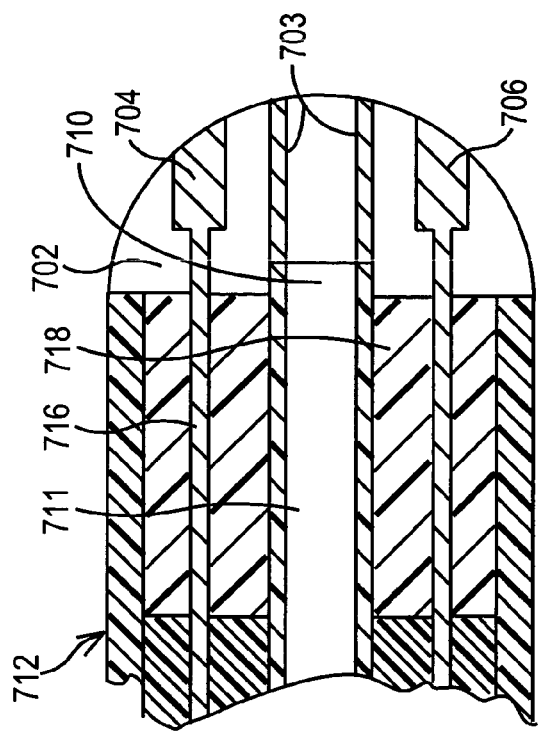
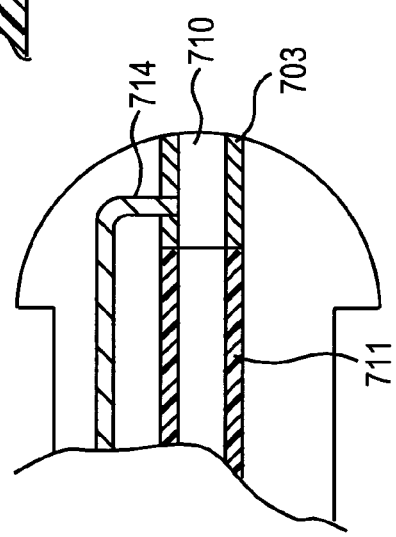
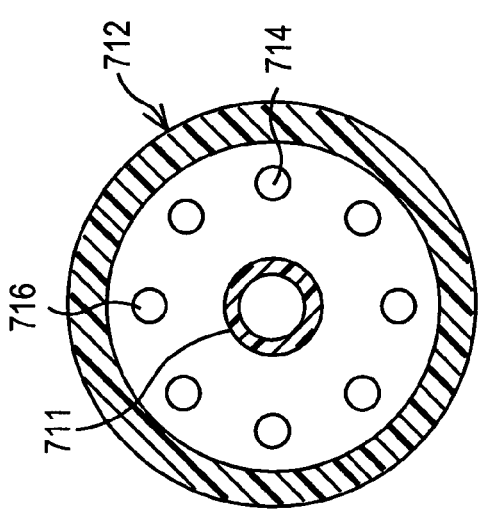

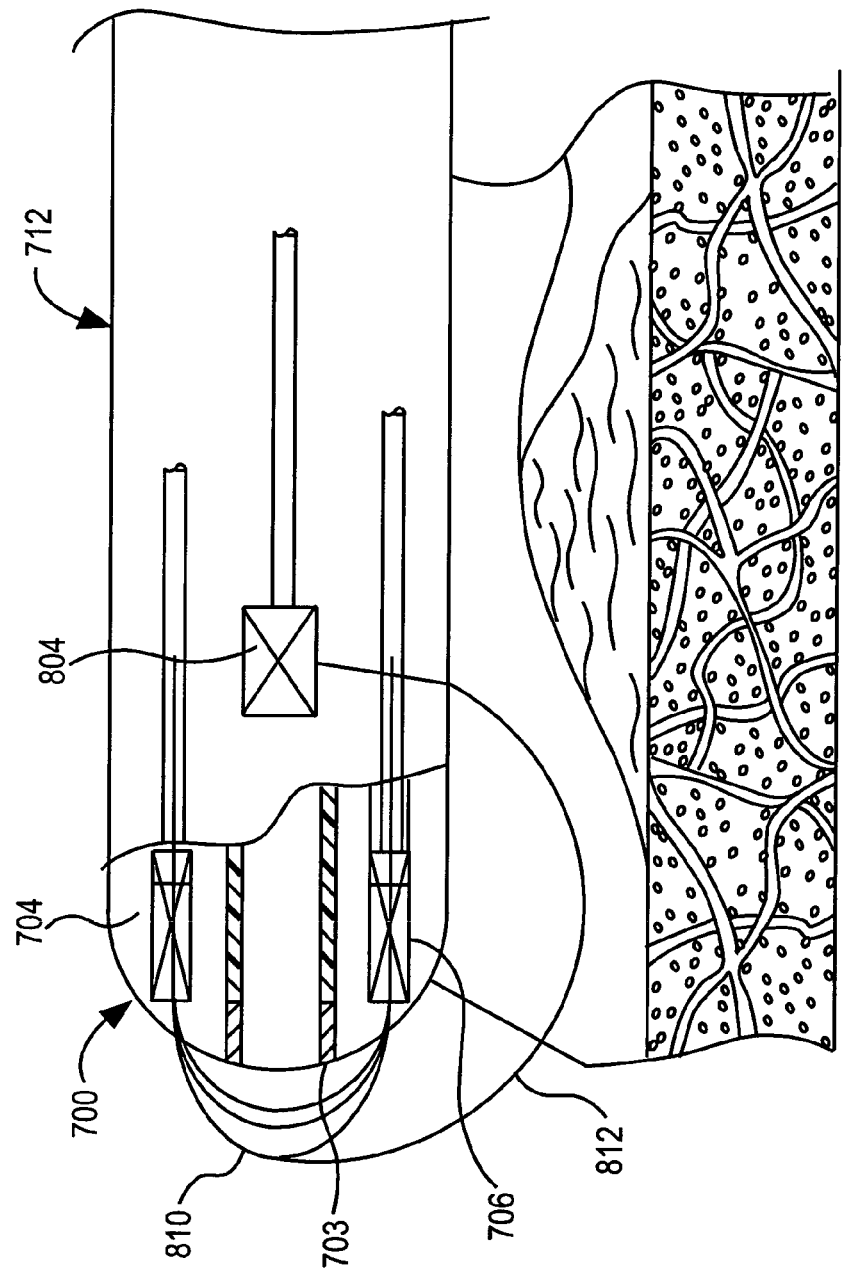

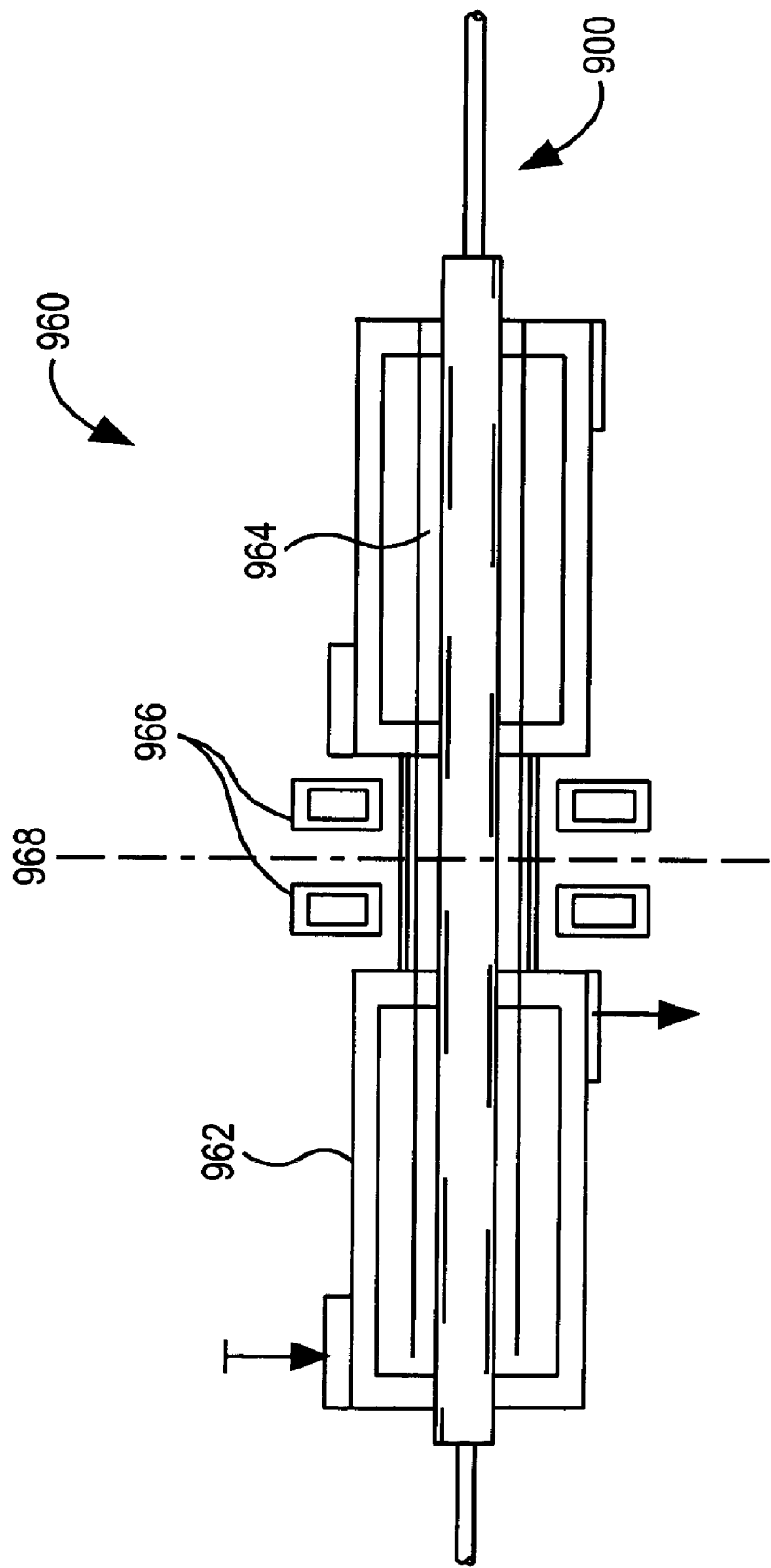

`US 7,311,702 B2`

ABLATION TECHNOLOGY FOR CATHETER BASED DELIVERY SYSTEMS

CROSS-REFERENCE TO RELATED APPLICATIONS

This application claims the benefit of U.S. provisional application Ser. No. 60/349,813, filed Jan. 18, 2002, the teachings of which are incorporated herein by reference.

FIELD OF THE INVENTION

The present invention relates generally to ablation technology, and in particular to a means for including such ablation technology in a catheter based delivery system. Such ablation technology can be controlled so that only specific targeted tissues are affected and non-targeted tissues are spared.

BRIEF DESCRIPTION OF THE DRAWINGS

Advantages of the present invention will be apparent from the following detailed description of exemplary embodiments thereof, which description should be considered in conjunction with the accompanying drawings, in which:

FIG. 1 is a catheter based delivery system consistent with the present invention;

FIG. 2 is a more detailed break away view of the dielectric tip, shrink tubing, and extrusion catheter body portion of the catheter based delivery system of FIG. 1;

FIG. 3 is an exploded view of a dielectric tip consistent with the present invention coupled to shrink tubing;

FIG. 4A is an internal view of the components of the dielectric tip of FIG. 3;

FIG. 4B is a plan view taken along the line 4B-4B of FIG. 4A;

FIGS. 9a-9c are various cross-sectional views illustrating arrangements of electrical conductors in the distal tip of FIG. 7;

FIG. 12 illustrates an exemplary emitted RF energy pattern provided using distal active electrodes consistent with the present invention;

FIG. 18 schematically illustrates an exemplary RF heating apparatus for assembling segmented catheter assembly consistent with the present invention.

DETAILED DESCRIPTION

Figure 5C:
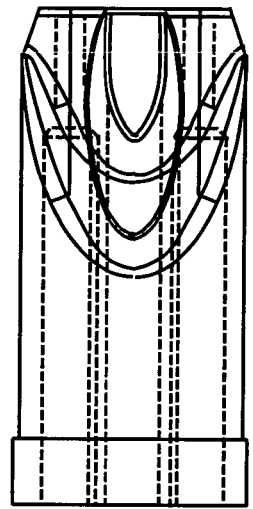
FIGS. 5A-5E are varying views of a dielectric tip consistent with the present invention.
Figure 5E:
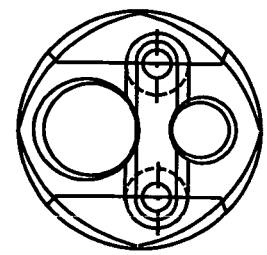
Figure 5D:
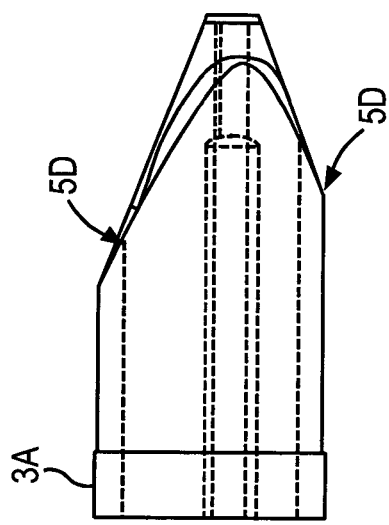
Figure 5A:
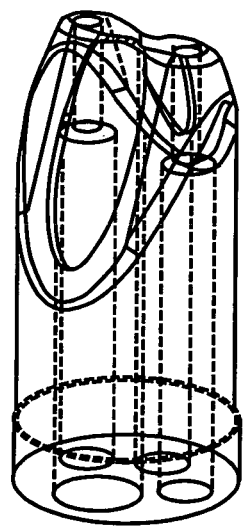
Figure 5B:
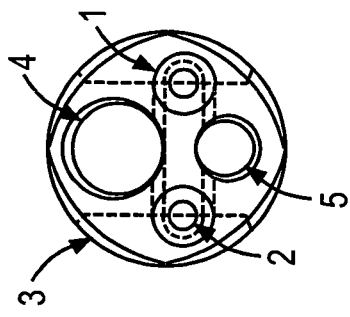

Consistent with one embodiment of the present invention, two electrodes may be configured in a side-by-side configuration such that one electrode functions as the active electrode and the other electrode functions as a return electrode, therein forming a closed-loop system. An electro surgical (ES) generator may be constructed so that as current passes from the active electrode to the return electrode the impedance of the tissue or material making contact with the two electrodes is detected. As this impedance information is gathered at a very high frequency, it is essentially providing real-time feedback to the generator as to the type of tissue the electrodes are contacting. Algorithms in the generator can be configured so that power settings used are constantly varied or optimized to the type of tissue being encountered by the two electrodes. Should non-target tissue types be encountered by the electrodes, the generator can immediately adjust power settings to low or null values to avoid unwanted effects to non-target tissues.

Turning to FIG. 1, a catheter based delivery system 100 consistent with the present invention is illustrated. The catheter system 100 includes a handle 9 and a power cord 10a that may be coupled back to an electro surgical generator (not shown) via an appropriate termination device 10b. The system 100 may also include a surgical irrigation line 8a and associated fitting 8b. The handle 9 may be further coupled to a dielectric tip 3 via an extrusion catheter body 7, e.g., a polyurethane 8 French (0.105 inch diameter) body and a shrink tubing 6, e.g. a high strength polyester shrink tubing, as more clearly illustrated in FIG. 2.

Turning to FIG. 3, a dielectric tip subassembly 300 is illustrated. The dielectric tip subassembly 300 includes the dielectric tip 3 coupled to the shrink tubing 6. Two electrodes 1 and 2 may be mounted as illustrated in a small diameter and relatively short length dielectric tip 3. In one exemplary embodiment, the small diameter may be 0.100 inches and the length of the dielectric tip 3 may be 0.250 inches. The dielectric tip 3 may be made of high temperature withstanding material such as alumina, zirconia, or others. Alternatively, the dielectric tip 3 may also be formed from more conventional materials, such as molded plastic. The electrodes 1 and 2 may be mounted flush to the surface of the dielectric tip 3 or may extend a minimal distance, e.g., 0.030 inches, from the distal tip of the dielectric tip 3.

Turning to FIG. 4A, an internal view of the components of the dielectric tip of FIG. 3 is illustrated. The first electrode 1 may be coupled to a stripped distal portion 1A of a small diameter conductor (not shown). Similarly, the second electrode 2 may be coupled to a similar stripped distal portion 2A. These individual conductors and the electrode connections may then be potted into the dielectric tip 3, e.g., using a high-temperature adhesive. The conductors may be insulated, and remaining proximal length of the insulated conductors may be twisted about each other to minimize electrical/electromagnetic effects and may be covered with a shield conductor. The bundles may be loaded through a large lumen 9 of the extrusion catheter body 7. In one example of many, the extrusion catheter body 7 may be a multi-lumen polyurethane 8 French (0.105 inch) extrusion catheter body.

The dielectric tip subassembly 300 may be mechanically attached to the catheter body 7 by heat-shrinking a very thin wall, e.g., about 0.001 inch, and the shrink tubing 6 around both the catheter body 7 and the dielectric tip subassembly 300. Adhesives may also be used to seal and supplement this joint. The dielectric component may also contain rings or undercuts 3A to enhance the grip of the shrink tubing 6.

Additional lumens may exist in the dielectric tip 3 for the passage of a guide wire, and to allow for suction or irrigation of the area surrounding the electrodes to remove tissue debris, or to allow the irrigation of the area with a solution for cooling the work area, or to enhance visualization techniques by the delivery of contrast or other agents, or to enhance conductivity or to enhance tissue differentiation in the work area. Lumens may be preferably configured to be in close proximity to the electrodes 1 and 2 to focus on the work area between the two electrodes for enhanced efficiency.

Figure 6:
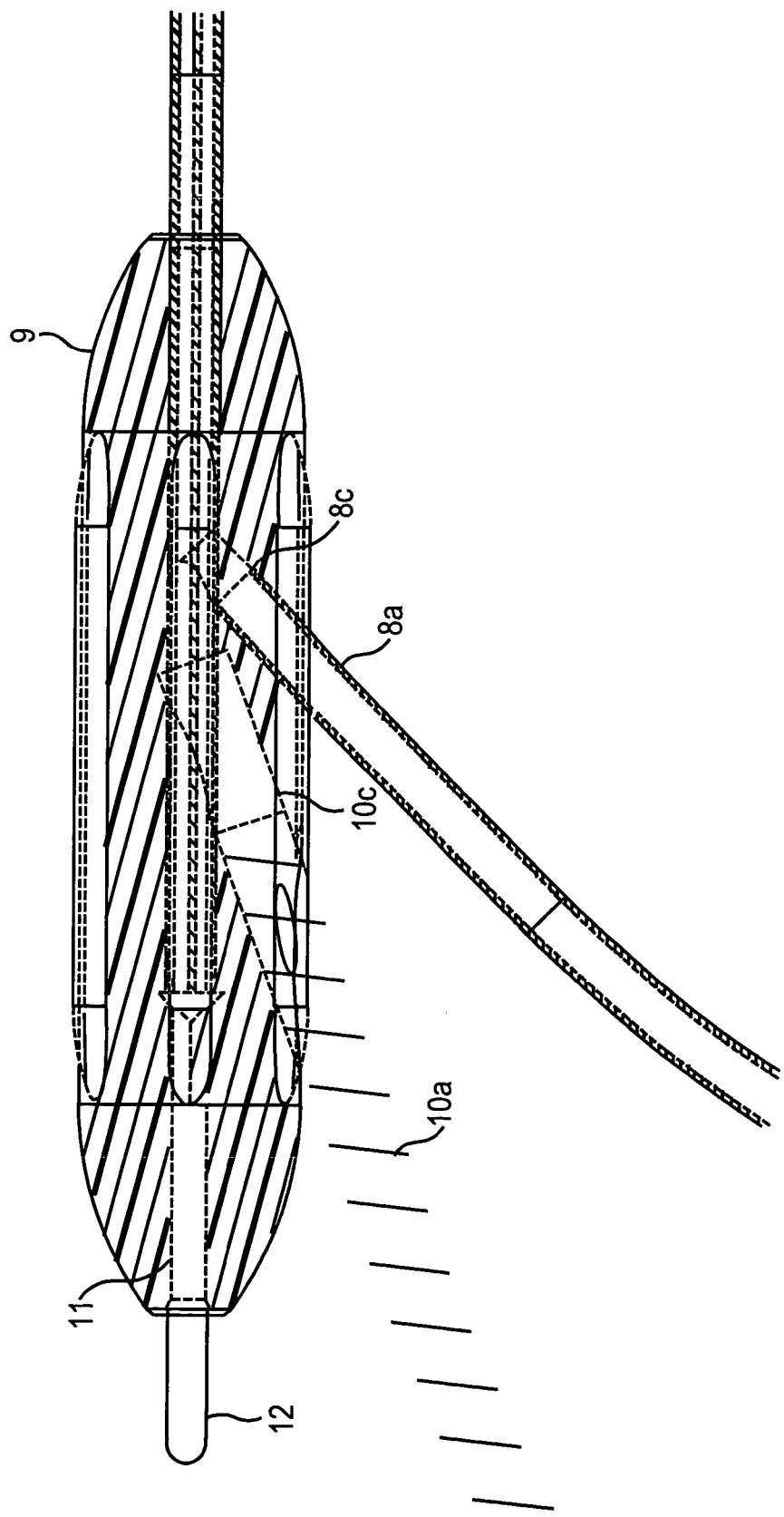
FIG. 6 is a cross sectional view of a handle and other associated parts which may be utilized as the handle in the catheter based delivery system of FIG. 1.

Turning to FIG. 6, a cross sectional view of exemplary handle 9 and other associated parts which may be utilized as the handle in the catheter based delivery system 100 of FIG. 1 is illustrated. The handle 9 terminates the proximal portion of the catheter. The handle 9 may be plastic and may have a thru lumen 11 for the passage of a guide wire. An additional angled lumen 10*c* may house the connection of the conductors to the power cord 10*a*. The power cord 10*a* may connect back to an electro surgical generator via an appropriate termination device 10*b* (see FIG. 1).

An additional angled lumen 8*c* may house and establish fluid communication with a suction/irrigation line and fitting 8*b*. The guide wire may be removed when ES energy is applied to the catheter thus also exposing this lumen for the creation of an inflow and out-flow fluid management system. This should allow for maximum control of temperature in the work area during delivery of ES energy.

Consistent with a second embodiment of the present invention the electro surgical generator may be a di-polar RF generator, such as produced by Nuvotek. The catheter based delivery system consistent with this embodiment of the invention includes an RF transmission and/or reception antenna disposed in a catheter. The surgical RF generator is constructed so that, in conjunction with the catheter based delivery system, RF energy having a controlled waveform may be transmitted in a controlled energy pattern. Preferably the system is constructed to enable multiplexing of the catheter delivery system, thereby allowing it to transmit and receive multiple RF wave forms. This ability may allow the use both for diagnostic and therapeutic applications.

When applied to diagnostic applications the invention provides imaging by transmitting an RF energy pattern and receiving a signal corresponding to type and proximity of surrounding tissue, bone, fluid, etc. The electro surgical generator transmits RF energy via the catheter based delivery system and receives a signal representative of the impedance associated with the biological material adjacent to a distal tip of the catheter delivery system. The received signal may be compared with known values of impedance associated with various biological materials, such as arterial wall or plaque formation, and provide an output indicative of the biological material. Furthermore, a proximity of the various detected biological materials relative to the distal tip of the catheter may further provide imaging of the interior of the cavity, vein, artery, etc., as well as biological composition. This imaging may be accomplished in real time or "near real time".

As applied in therapeutic application, this embodiment of the present invention may be used to ablate specific biological materials, such as plaque formations within an artery, tumors, or other biological material to be ablated, without producing extensive damage of surround non-targeted tissue. The RF generator is employed to transmit, via the catheter based delivery system, RF energy having a waveform configured to ablate only the specific targeted tissue. This therapeutic application may be carried out in real time, especially when used in conjunction with diagnostic/imaging feature and utilizing multiplexing capability of the catheter based delivery system.

Consistent with the objective of transmitting RF energy and also receiving a signal representative of adjacent tissue, the distal tip may be configured to function as an antenna. One such suitable antenna configuration may be a Yagi-Uda antenna arrangement; although those having skill in the art will readily appreciate that numerous other antenna arrangements may be suitable. According to the Yagi-Uda antenna model, an exemplary embodiment may include an emission electrode for the RF generator adjacent a catheter distal tip, at least one electrode configured to act as a director electrode, and at least one electrode configured to act as a reflector electrode. RF energy may be transmitted from the emission electrode in an energy pattern controlled by the director and reflector electrodes. It will also be understood by those having skill in the art that different antenna configurations may require different configurations of conductors in the catheter. For the clarity of description of this embodiment, however, an exemplary catheter based delivery system utilizing a Yagi-Uda model antenna will be discussed.

Figure 7:
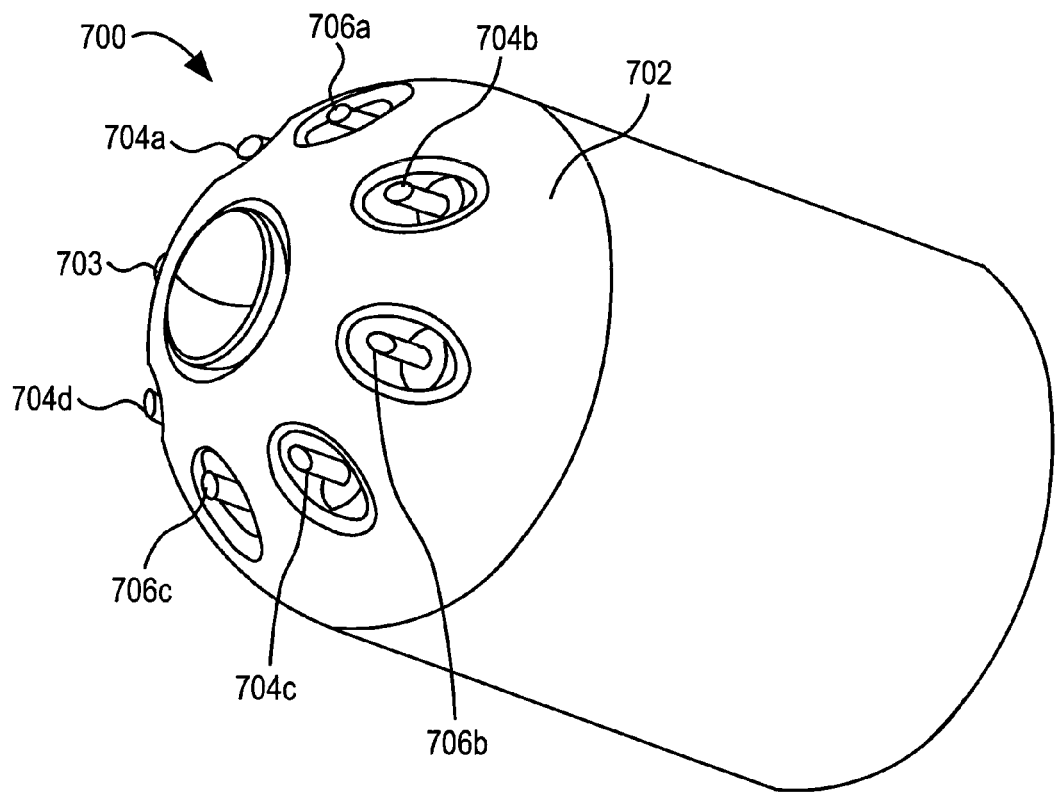
FIG. 7 is a perspective view of a catheter distal tip consistent with the present invention.
Figure 8:
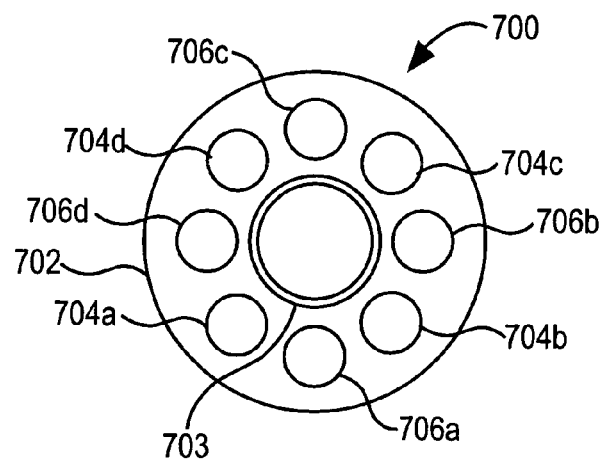
FIG. 8 is an end view of the distal tip of FIG. 7.

Turning to FIGS. 7 and 8, a distal tip 700 of a catheter based delivery system consistent with the second embodiment of the present invention is illustrated in perspective view and end view respectively. The distal tip 700 includes a dielectric body 702, and emitter electrode 703, and four each director electrodes 704*a-d* and reflector electrodes 706*a-d*. While the catheter based delivery system may be sized according to specific applications, advantageously the distal tip 700 has a diameter of 8 French or less, desirably 4 French. Sizes of the catheter delivery system in this range can provide intravascular access to most areas of the body.

It should be understood that greater of fewer reflectors and directors may be utilized according to specific application and tip size, while still adhering to the principles of the present invention. Similarly, it should be understood that the director electrodes and reflector electrodes do not need to be arranged in discrete pairs including an adjacent director electrode and reflector electrode. Consistent with the illustrative Yagi-Uda antenna model, an emitted RF energy pattern may be provided by an emitter in conjunction with an electrode active pair including a director electrode and a reflector electrode. The shape of the RF pattern will be influenced by the relative positions of the respective director electrode and reflector electrode. Accordingly, the energy pattern may be altered by controlling the specific director electrode(s) and reflector electrode(s) utilized as the active pair(s).

The embodiment illustrated in FIG. 7 shows the director electrodes 704*a-d* and the reflector electrodes 706*a-d* disposed in pockets or recesses 708 in the distal tip 700. It is possible that the recesses 708 may be susceptible to collecting debris or becoming clogged with other matter. Consistent with alternative embodiments the director electrodes 704*a-d* and the reflector electrodes 706*a-d* may be disposed in the distal tip 700 such that the terminal ends of each electrode is generally flush with the outer surface of the dielectric body 702. The flush configuration of the electrodes 704 and 706 may avoid such specific drawbacks associated with the embodiment illustrated in FIG. 7.

Referring to FIGS. 9a through 9c, a cross-sectional view of the exemplary distal tip 700 is illustrated. The emitter electrode 703 may be a conductive, tubular member received in the dielectric body 702 such that the opening of the emitter electrode 703 is aligned with a central lumen 710 defined by a common core 711 of the catheter body 712. As best seen in FIG. 9b, the emitter electrode may be electrically coupled to a conductor 714. Preferably, the conductor 714 is loaded through the catheter body 712 offset from the central lumen 710. This configuration may be used to leave the central lumen 710 available for a guide wire, or similar apparatus. Each of the director electrodes 704 and reflector electrodes 706 are similarly disposed in the dielectric body 702 and electrically coupled to respective conductors carried in respective individual radial lumens 716 and 718 of the catheter body 712. Alternatively, the conductors coupled to the individual director and reflector electrodes 704 and 706 may be bundled carried in a common lumen or several lumens each carrying more than one conductor.

According to one embodiment of the general Yagi-Uda antenna model, each of the director electrodes 704 may include a capacitor disposed in the dielectric body 702 of the distal tip, and each of the reflector electrodes 706 may include an inductor disposed in the dielectric body 702 at the distal tip 700. However, the use of a capacitor associated with the director electrode 704 and the use of an inductor associated with the reflector electrode may be reversed, or eliminated though conventional adjustments in the software and/or hardware of the system, while still maintaining the general exemplary Yagi-Uda antenna configuration.

To achieve the desired operation of the center emitter 703, the director electrode 704, and the reflector electrode 706 as an antenna, it may be advantageous to arrange the electrodes such that the distal end of the director electrode 704 and distal end of the reflector electrode 706 to have a −Z offset relative to the distal end of the center emitter electrode 703. That is, it may be desirable that the distal ends of the director electrode 704 and the distal end of the reflector electrode 706 are positioned proximally on the catheter tip 700 relative to the center conductor 703. A desired degree of offset may be achieved by providing the distal tip 700 having a rounded configuration, such as a hemisphere or ellipsoidal shape. This configuration has been variously illustrated in the preceding drawings. Such a rounded end configuration may additionally facilitate smooth advancement of the catheter delivery system as it is pushed through a vein, enhance blood flow-stream recombination, etc.

Figure 10A:
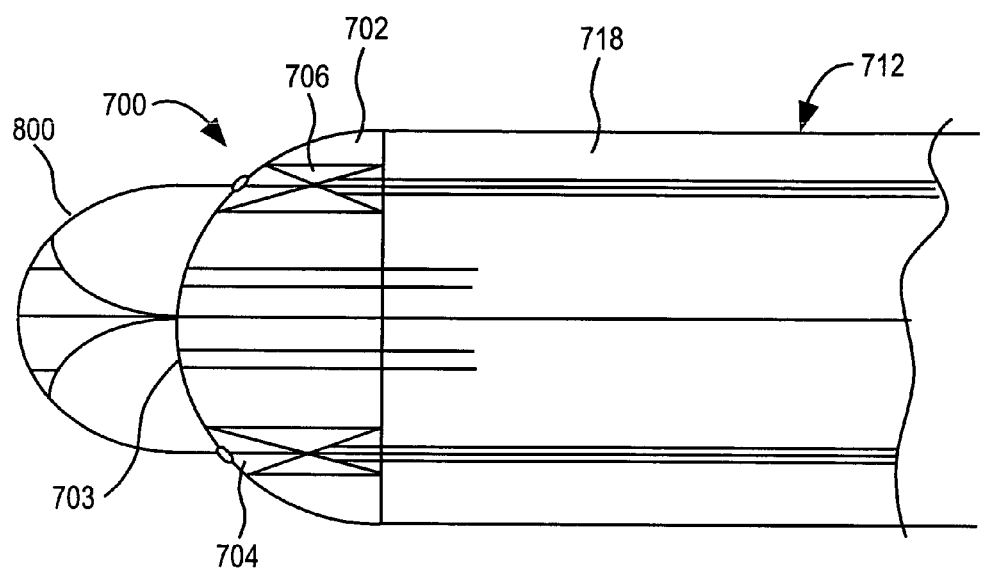
FIGS. 10a-10b illustrate a first exemplary emitted RF energy pattern consistent with the present invention.
Figure 10B:
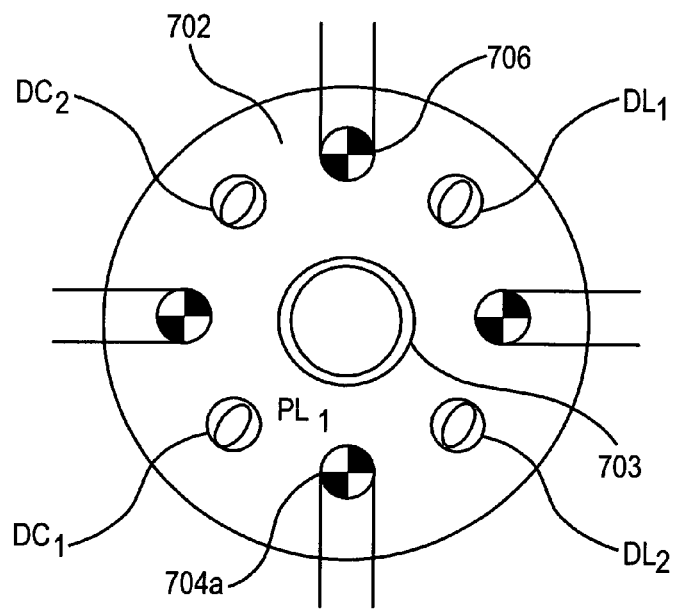

Referring to FIGS. 10a and 10b, a cross-sectional view and an end view of an exemplary distal tip 700 consistent with the catheter based delivery system of the present invention. FIG. 10a illustrates an exemplary emitted RF energy pattern produced by the interaction of the center emitter 703, a director electrode 704 and a reflector electrode 706. Consistent with this illustrated embodiment, the dielectric body 702 may include an RF shielding material, exposing only the very ends of director electrode 704 and reflector electrode 706 for interaction with the emitted RF field. Accordingly, as illustrated the emitted RF pattern may be predominantly forward looking, i.e., the radiation pattern may be directed predominantly ahead of the distal tip 700, rather than laterally therefrom.

Figure 11A:
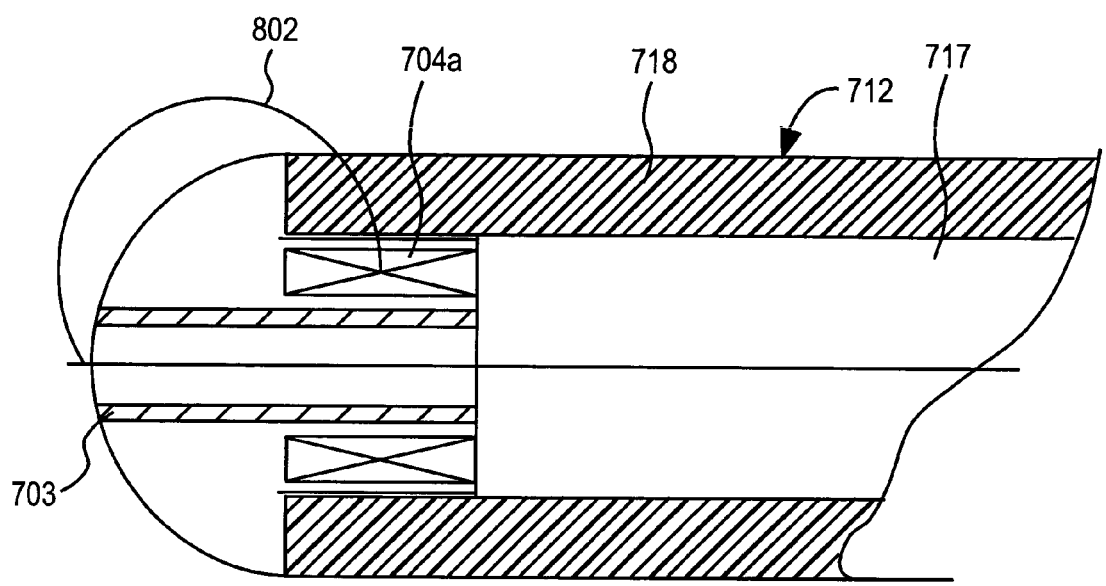
FIGS. 11a-11b illustrate a second exemplary emitted RF energy pattern consistent with the present invention.
Figure 11B:
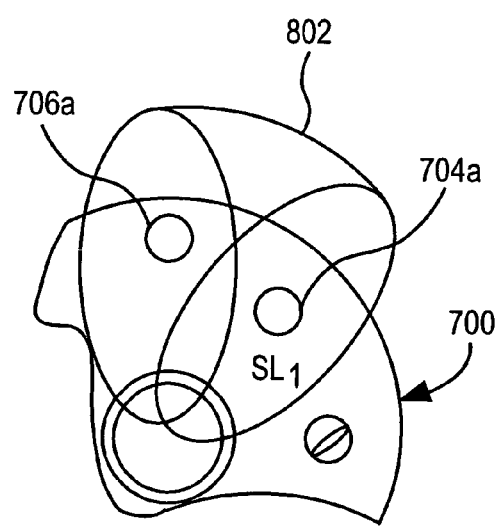

Referring to FIGS. 11a and 11b, a directional RF energy pattern 802 may be produced, as is especially evident in the partial end view of FIG. 11b. The directional RF pattern 802 may be produced by employing director electrode 704a and adjacent reflector electrode 706a. The resultant directional RF pattern 802 may be produced having a generally wedge shaped profile, as described from an end view of the distal tip 700. The angular expanse of the directional RF pattern 802 may be related to the angular separation of the director electrode 704 and reflector electrode 706 employed in generating the RF pattern. Accordingly, if adjacent and closely space director and reflector pairs are used in generating the RF pattern, the resultant directional pattern may have a relatively narrow, or highly directional character. Conversely, if widely spaced and/or non-adjacent director and reflector pair are employed, a more broad and/or less directional RF pattern may result. The active pair of electrodes, i.e., the director electrode and reflector electrode employed in generating an RF pattern may be selected by an operator to achieve the desired pattern. Furthermore, it may be possible to simultaneously select several active pairs to generate a broad pattern, or optionally several radially spaced patterns.

As best illustrated in FIG. 11a, it may also be possible to achieve a lateral projection, or side-looking character in the RF pattern 802. This aspect may be achieved by providing a sheath 718 of catheter body 712 that is at least partially RF transparent within the utilized range. Accordingly, as illustrated the RF pattern may be provided between the emitter 703 and a side portion of an active electrode, for example director electrode 704a, rather than only an end portion of an active electrode.

Consistent with an alternative embodiment, a sliding sheath may be provided at the distal tip of the catheter delivery system. The sliding sheath may be constructed to act as an RF shielding around the director electrodes and the reflector electrodes. When the sliding sheath is provided in a distally advanced position, the shielding effect of the sheath may permit only a very end portion of an active electrode to influence the RF pattern, thereby producing a generally forward looking pattern, such as the pattern illustrated in FIG. 10a. However, if the sliding sheath is proximally retracted, a side portion of an active electrode may be available to influence the RG pattern, thereby providing a more side looking component to the RF pattern, such as the pattern illustrated in FIG. 11.

Referring to FIG. 12, a catheter based delivery system may further be provided with one or more proximal director electrodes 804 and proximal reflector electrodes 806 in addition to the distal director electrodes 704 and reflector electrodes 706. The proximal electrodes 804, 806 may operate to provide an RF energy pattern 812 extending from the distal emitter electrode 703 proximally toward electrodes 804 and 806. Proximal director electrodes 804 and reflector electrodes 806 may be of a similar character as the distal director electrodes 704 and distal reflector electrodes 706. That is, the proximal electrodes 804, 806 may respectively include capacitor elements and inductor elements. As illustrated, the proximal energy pattern 812 provided using the proximal active electrodes 804 and 806 may be largely side looking, and may provide a greater portion of the energy pattern 812 in a region proximal to the distal tip 700. This proximal energy pattern 812 may be employed in conjunction with a distal energy pattern 810 provided using the distal electrodes 704 and 706, as discussed previously.

As with the distal electrodes 704 and 706, a plurality of each proximal director electrodes 804 and proximal reflector electrodes 806 may be arranged about the circumference of the catheter body 712. The selective activation of individual proximal electrodes may be employed to provide directionality to the energy pattern 812, in a manner similar to that discussed with reference to FIGS. 11a and 11b. Proximal electrodes 804 and 806 may be distributed axially along the catheter 712 as well as circumferentially. Axial distribution of the proximal electrodes 804 and 806 may be used to provide varying available energy patterns.

It will be apparent to those having skill in the art that the various above-described RF energy patterns, i.e., forward looking, side looking, directional, etc., may be achievable through various other means. Alternative means for achieving desired emission/reception patterns may include modifications to various hardware components, software components, and/or differing antenna designs.

Figure 13:
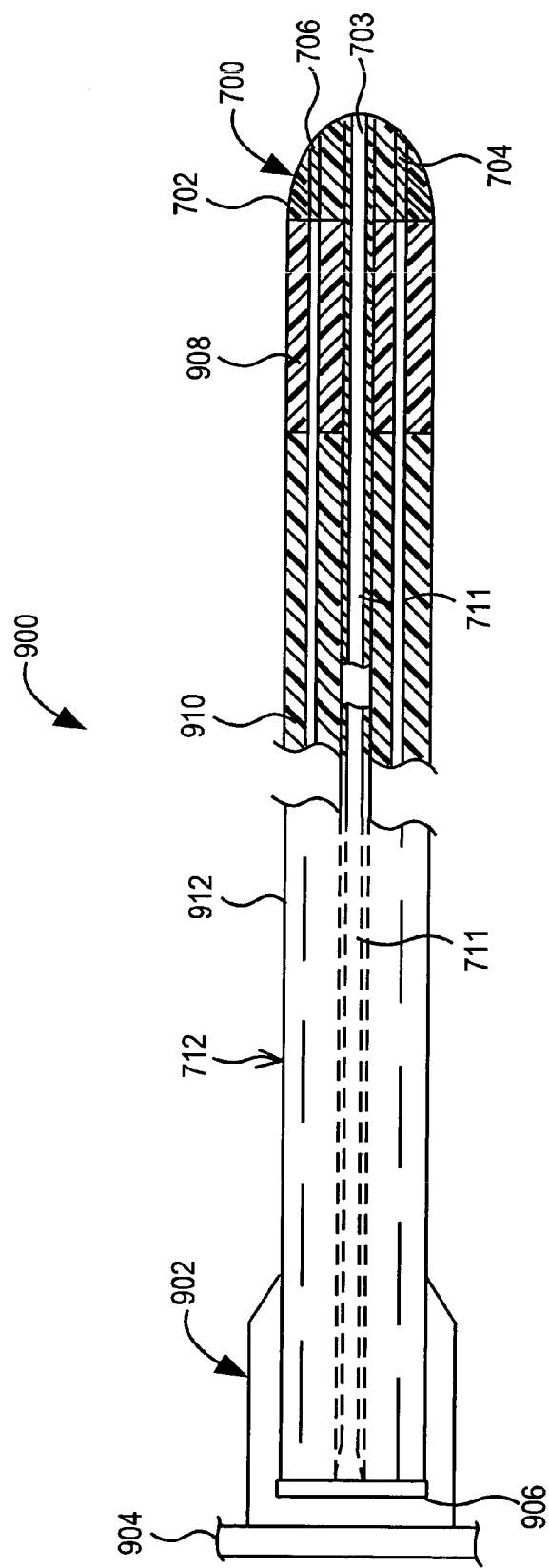
FIG. 13 is a cross-sectional view of an exemplary catheter assembly consistent with the present invention.

Turning next to FIG. 13, a catheter assembly 900 consistent with one embodiment of the present invention is generally shown including distal tip 700, catheter body 712 and proximal end 902. The distal tip 700 may include a dielectric body 702 having a center emitter electrode 703, director electrode 704 and reflector electrode 706, as previously discussed. The catheter body may include any conventional catheter configured to be coupleable with the dielectric body 702 and to carry the necessary conductors. According to the illustrative embodiment, the catheter body 712 may include a common central core 711 running the length of the catheter assembly 900. Advantageously, the common central core 711 includes a lumen extending through the center emitter electrode 703. The proximal end 902 may include a coupling means 904, such as a conventional luer fitting, for coupling the catheter assembly 900 to additional apparatus. Additionally, the proximal end 902 may include an electrical connection 906 terminating the through-catheter conductors for the emitter electrode 703, the director electrode 704, and the reflector electrode 706 and providing electrical connection, for example, to a surgical RF generator.

According to an exemplary embodiment, the catheter assembly 900 may employ a segmented and/or laminated thermoplastic polyurethane catheter 712. Alternatively, the catheter 712 may be formed from any other polymeric material, as is conventionally utilized for producing catheters. As illustrated in FIG. 13, the catheter 712 may include a continuous core 711 having multiple segments 702, 908, 910, 912 disposed axially over the core 711. The physical, mechanical, chemical, etc., properties of the various components may be controlled to provide varying or multiple characteristics at different portions of the catheter assembly. Consistent with one exemplary configuration, continuous core 711 may be a high modulus/high durometer material, such as a polyurethane tube having a durometer of 72 on the Shore D scale. The distal end of the core 711 may be coupled to the dielectric body 702 of the distal tip 700. The proximal end of the core 711 is preferably coupled to the proximal end 902 of the catheter system. Disposed over the core 711 adjacent the distal tip 702 may be a soft segment 908, e.g., having a durometer of 85 Shore A. Segments 910, 912 having progressively higher moduli toward the proximal end 902 may be disposed over the core 711. This structure may provide a single continuous catheter assembly 900 having an axially varying modulus/durometer. In the case of the described embodiment, the distal region of the catheter may be relatively soft and flexible, thereby minimizing trauma associated with introducing the catheter assembly 900 in to a vein, artery, etc., and improving the track-ability. Similarly, the rigid center core 711 may improve the torqueability of the catheter system, i.e., improve the ability to rotate the distal end of the catheter by rotating the proximal end of the same, without necessitating a biaxial sheath over the catheter. The result may be a catheter having increased torsional stiffness, but increased axial flexibility.

Figure 14:
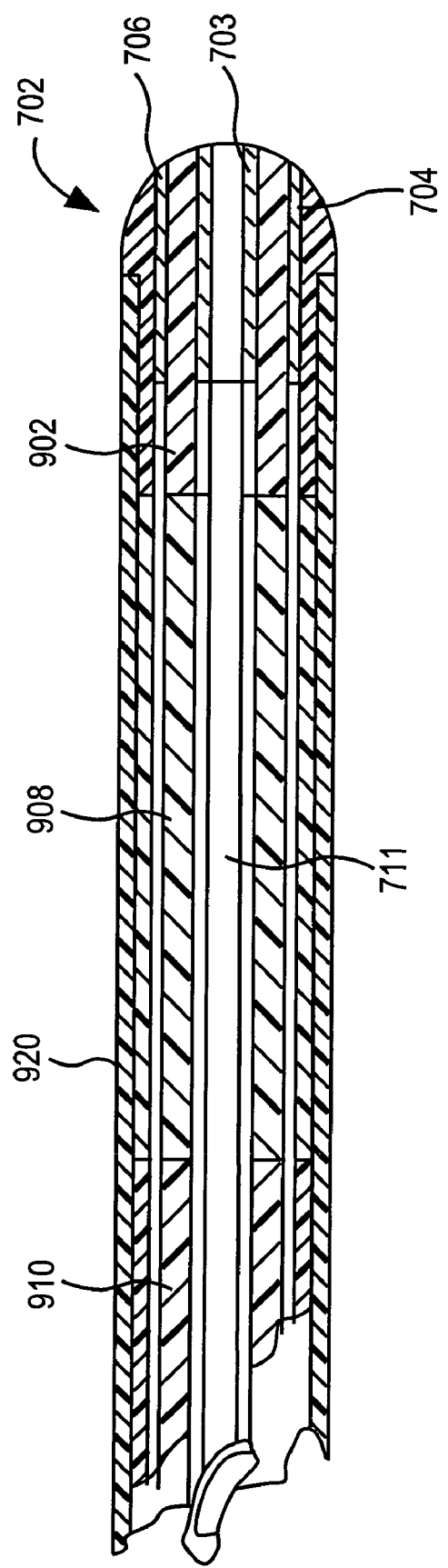
FIG. 14 is a cross-sectional view of a distal portion of an exemplary catheter assembly consistent with the present invention.

Turning to FIG. 14, a portion of the distal end of the catheter assembly 900 is illustrated in cross-section. As with the previous embodiment, the catheter may include a dielectric body 702 having center core 711 with increasing durometer axial segments 908 and 910 disposed over the core 711. An outer sheath 920 may then be disposed over the axial segments 908, 910. The outer sheath may be soft or hard depending on the required characteristics of the catheter. Additionally, the character of the sheath may be manipulated to provide different surface characteristics of the catheter, such as reduced surface tension, a tacky surface, etc.

In addition to being axially segmented, the catheter may also, or alternatively, include coaxial layers laminated together. The coaxial laminations may extend the entire length of the catheter system. Alternatively, the coaxial laminations may only be present in individual axial segments, or groups of segments.

Figure 15:
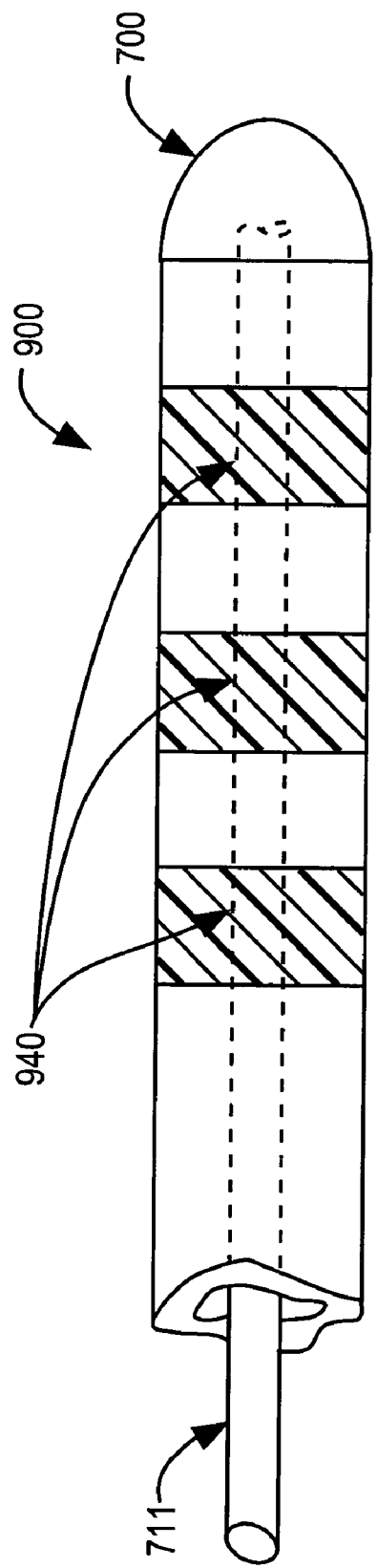
FIG. 15 illustrates a segmented catheter assembly consistent with the present invention.

Segments may also be incorporated into the catheter assembly 900 to aid in the positioning of the catheter. For example, one or more radiopaque segments may be incorporated to allow the catheter to detected using conventional radiological examination. As illustrated in FIG. 15, more than one radiopaque segments 940 may be used in sequence to improve detection of the catheter assembly 900. The radiopaque segments may be employed only near the distal end 700 of the catheter assembly to allow radiological detection of the distal end. Alternatively, various portions of the catheter assembly 900 may include radiopaque segments 940 to better allow the path of the catheter to be tracked. Along these lines, the various portions of the catheter assembly 900 may include different patterns of radiopaque segments 940 to identify individual portions of the catheter assembly. The radiopaque segments 940 may be formed from a polymer material incorporating a radiopaque filler. Exemplary radiopaque fillers may include tungsten or barium compounds. Various other suitable materials known to those having skill in the art may also be used to impart radiopacity. Given the potential for biological interaction with some variety of know radiopaque materials, it may be desirable to provide a coaxial sheath layer, such as that previously disclosed, disposed over the radiopaque segments to isolate the radiopaque material from direct physiological contact.

In addition to providing radiopaque segments that may allow radiological detection of the catheter assembly inside the body, the catheter assembly may include visually discernable indicia providing information about the placement of the catheter. For example, the catheter may be provided with periodic circumferential bands representative of a distance to the tip. This information may be used to determine length of catheter penetration. The exemplary bands may be provided having pattern and/or color representative of linear position of the catheter. Similarly, the catheter may include axially arranged indicial, such as an axial stripe, that may be indicative of rotational orientation. Various other information may be represented using visual indicia, as will be apparent to those having skill in the art. The visually discernable indicial may be integrated into the catheter assembly via the segmentation/lamination construction. For example, colored segments may be integrated into the catheter assembly. Alternatively, indicia may be printed on the catheter assembly, either on an outer layer of the catheter, or beneath transparent/translucent outer layers.

A segmented and/or laminated catheter assembly consistent with the present invention may be produced by applying the various segments and/or coaxial layers over a center mandrel or a center core, which may itself be supported by a mandrel, and joining the individual components about the interfaces thereof. Solvents are used to temporarily swell the polymer segments sufficient to allow the individual segments to be threaded onto a core or a supporting mandrel if a core is not used. The particular solvents used will vary depending upon the polymer employed in the various segments. Appropriate solvents for different polymers are known to those having skill in the art. In the example of thermoplastic polyurethane, isopropyl alcohol may be used as a suitable solvent. Once the segments have been positioned, the solvent may be removed by evaporation or by rinsing, for example in water.

Any conductors that are to be loaded through the catheter may be threaded through corresponding lumens in the individual segments at the same time the segments are being threaded onto the core or support mandrel. In this manner, continuous conductors may be used, threaded through the various segments from the proximal end of the catheter to the distal end. The use of continuous conductors eliminates the potential problems associated with numerous electrical connections that would otherwise be necessary.

Figure 16:
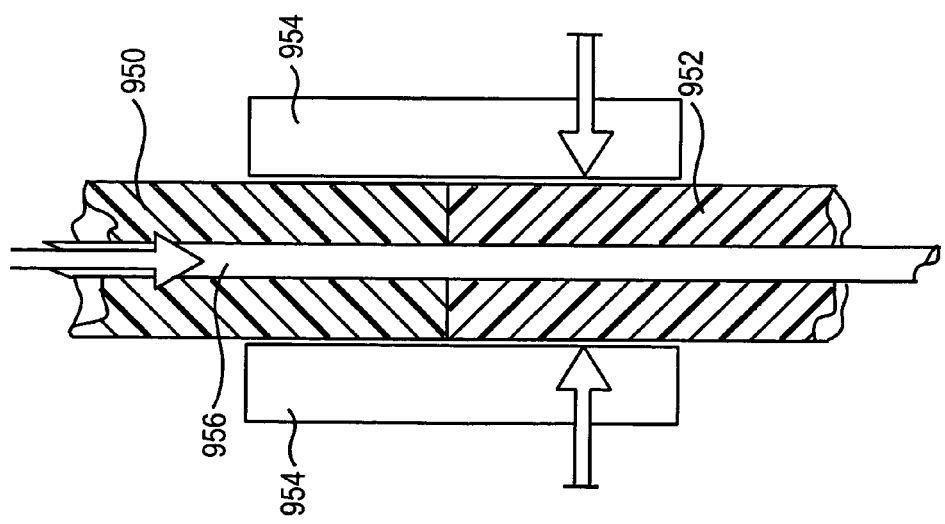
FIG. 16 illustrates an exemplary die assembly that may be used for assembling a segmented catheter assembly consistent with the present invention.

Referring to FIG. 16, after a first segment 950 and a second segment 952 have been threaded on a supporting core or mandrel 956, the segments 950 and 952 may be joined at the interface thereof. Suitable methods of joining the segments 950 and 952 may include thermal welding, sonic welding, solvent bonding, solvent welding, etc. In the illustrated example, the segments 950 and 952 are supported in a die 954 and heated in thermally weld the segments 950 and 952. Advantageously, one segment 950 may be clamped sufficiently to prevent axial movement, while axial pressure is applied to the second segment 952, urging the second segment 952 toward the first 950 during the thermal welding process, thereby enhancing the inter-segment bond.

Figure 17A:
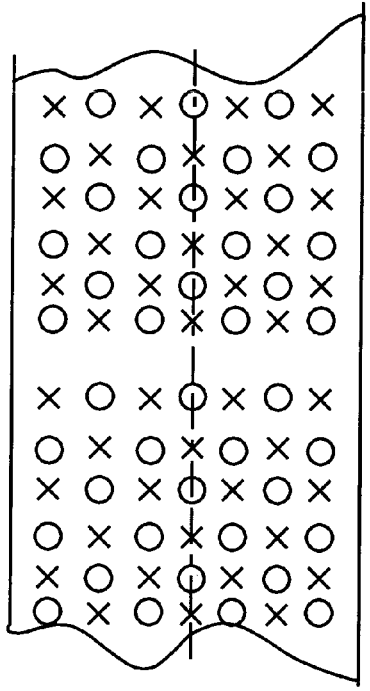
FIGS. 17a-17b respectively representationally illustrate stress-relieved catheter segments and non-stress-relieved catheter segments.
Figure 17B:
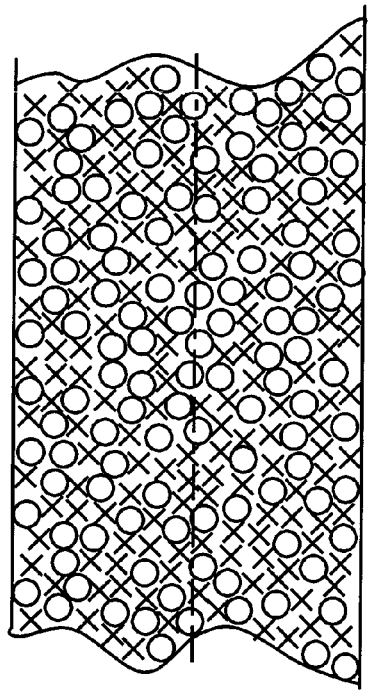

Advantageously, the welding cycle may be coordinated to simultaneously allow the polymer segments to orient into low stress configurations, and then cool to prevent residual stress build up. Such a process generally amounts to annealing the polymer segments. Annealed versus non-anneal structures are representationally illustrated in FIGS. 17*a* and 17*b* respectively. This optional annealing process may avoid warpage and other stress related defects that may occur.

Referring to FIG. 18, an exemplary die for forming a segmented and/or laminated catheter assembly 900 is shown at 960. A first die portion 962 and a second die portion 964 support respective catheter segments (not shown) about to be joined about a joint interface, indicated at 968. The respect die portions 962 and 964 may be water, or otherwise, cooled to minimize thermal transfer to portions of the catheter assembly 900 away from the joint site. The region of the joint interface 968 may be heated using RF induction coils 966 tuned to provide efficient heating of the polymers being joined, as will be appreciated by those having skill in the art. Desirably, the die portions 962 and 964 are constructed of a material that will minimize RF energy heat conduction to the enclosed segments, such as 4 series stainless steel.

The embodiments that have been described herein, however, are but some of the several which utilize this invention and are set forth here by way of illustration but not of limitation. It is obvious that many other embodiments, which will be readily apparent to those skilled in the art may be made without departing materially from the spirit and scope of the invention as defined in the appended claims.

What is claimed is:

1. A catheter based delivery system comprising:
 a catheter having a distal end;
 an emitter electrode disposed in said distal end and configured to emit RF energy, wherein a position of said emitter electrode is substantially fixed with respect to said distal end of said catheter;
 at least one director electrode disposed in said distal end, wherein a position of said at least one director electrode is substantially fixed with respect to said distal end of said catheter; and
 at least one reflector electrode disposed in said distal end, wherein a position of said at least one reflector electrode is substantially fixed with respect to said distal end of said catheter;
 said at least one director electrode and said at least one reflector electrode configured to control said RF energy and generate a desired emitted RF energy pattern proximate said distal end of said catheter.

2. A catheter based delivery system according to claim 1 wherein said at least one director electrode comprises a capacitor and said at least one reflector electrode comprises an inductor.

3. A catheter based delivery system according to claim 1, wherein said emitter electrode is centrally disposed in said distal end and said at least one director electrode and said at least one reflector electrode are disposed radially around said emitter electrode.

4. A catheter based delivery system according to claim 1 further comprising at least one director electrode disposed proximal said distal end.

5. A catheter based delivery system according to claim 4, wherein said at least on director electrode comprises a capacitor.

6. A catheter based delivery system according to claim 1 further comprising at least one reflector electrode disposed proximal said distal end.

7. A catheter based delivery system according to claim 6 wherein said reflector electrode comprises an inductor.

8. A catheter based delivery system comprising:
 a catheter having a distal end configured to transmit RF energy; and
 a Yagi Uda type antenna, comprising:
 an emitter electrode disposed in said distal end_and configured to emit RF energy, wherein a position of said emitter electrode is substantially fixed with respect to said distal end of said catheter;
 at least one director electrode disposed in said distal end, wherein a position of said at least one director electrode is substantially fixed with respect to said distal end of said catheter; and
 at least one reflector electrode disposed in said distal end, wherein a position of said at least one reflector electrode is substantially fixed with respect to said distal end of said catheter; said at least one director electrode and said at least one reflector electrode configured to control said RF energy and generate a desired emitted RF energy pattern proximate said distal end of said catheter.

9. A catheter based delivery system according to claim 8, wherein said at least one director electrode comprises a capacitor, and said at least one reflector electrode comprises an inductor.

10. A catheter based delivery system according to claim 8, wherein said catheter comprises an assembly of a plurality of joined individual tubular members.

11. A catheter based delivery system according to claim 10, wherein said plurality of tubular members are disposed axially along said catheter.

12. A catheter based delivery system according to claim 10, wherein said plurality of tubular members are co-axially disposed along said catheter.

13. A catheter based delivery system according to claim 1 wherein a distal end of said at least one director electrode and a distal end of said at least one reflector electrode are offset along a longitudinal axis of said catheter from a distal end of said emitter electrode.

14. A catheter based delivery system according to claim 1 wherein said distal end of said catheter comprises an at least partially RF transparent sheath disposed about at least a portion of said at least one director electrode and said at least one reflector electrode.

15. A catheter based delivery system according to claim 1 wherein said distal end of said catheter comprises an RF shielding sheath configured to move along a longitudinal axis of said catheter relative to said at least one director electrode and said at least one reflector electrode.

16. A catheter based delivery system according to claim 1 comprising at least one proximal director electrode and at least one proximal reflector electrode radially disposed about said distal end of said catheter.

17. A catheter based delivery system according to claim 1 wherein said emitter electrode, said at least one director electrode, and said at least one reflector electrode are substantially flush with an outer surface of said catheter.

18. A catheter based delivery system according to claim 8 wherein a distal end of said at least one director electrode and a distal end of said at least one reflector electrode are offset along a longitudinal axis of said catheter from a distal end of said emitter electrode.

19. A catheter based delivery system according to claim 8 wherein said distal end of said catheter comprises an at least partially RF transparent sheath disposed about at least a portion of said at least one director electrode and said at least one reflector electrode.

20. A catheter based delivery system according to claim 8 wherein said distal end of said catheter comprises an RF shielding sheath configured to move along a longitudinal axis of said catheter relative to said at least one director electrode and said at least one reflector electrode.

21. A catheter based delivery system according to claim 8 comprising at least one proximal director electrode and at least one proximal reflector electrode radially disposed about said distal end of said catheter.

22. A catheter based delivery system according to claim 8 wherein said emitter electrode, said at least one director electrode, and said at least one reflector electrode are substantially flush with an outer surface of said catheter.

* * * * *